United States Patent
Magni et al.

(10) Patent No.: US 10,682,161 B2
(45) Date of Patent: Jun. 16, 2020

(54) INNER FIXATION DEVICE FOR THE TREATMENT OF A LIMB, IN PARTICULAR THE FEMUR DISTAL PORTION OR TIBIA PROXIMAL PORTION

(71) Applicant: ORTHOFIX S.R.L., Bussolengo (IT)

(72) Inventors: Marco Magni, Ferrara (IT); Andrea Zaccaria, Tregnago (IT); Daniele Venturini, Povegliano Veronese (IT)

(73) Assignee: ORTHOFIX S.R.L., Bussolengo (IT)

( * ) Notice: Subject to any disclaimer, the term of this patent is extended or adjusted under 35 U.S.C. 154(b) by 0 days.

(21) Appl. No.: 16/096,135

(22) PCT Filed: Apr. 26, 2017

(86) PCT No.: PCT/EP2017/059952
§ 371 (c)(1),
(2) Date: Oct. 24, 2018

(87) PCT Pub. No.: WO2017/186802
PCT Pub. Date: Nov. 2, 2017

(65) Prior Publication Data
US 2019/0133643 A1    May 9, 2019

(30) Foreign Application Priority Data

Apr. 28, 2016  (IT) .................. 102016000043690

(51) Int. Cl.
*A61B 17/68*  (2006.01)
*A61B 17/80*  (2006.01)
*A61B 17/56*  (2006.01)

(52) U.S. Cl.
CPC .......... *A61B 17/683* (2013.01); *A61B 17/80* (2013.01); *A61B 17/8061* (2013.01); *A61B 2017/565* (2013.01)

(58) Field of Classification Search
CPC .............. A61B 17/683; A61B 17/8061; A61B 2017/565; A61B 2017/681
See application file for complete search history.

(56) References Cited

U.S. PATENT DOCUMENTS 6,302,887 B1 * 10/2001 Spranza .............. A61B 17/683
411/338
2003/0135212 A1 * 7/2003 Y. Chow ................ A61B 17/72
606/64

(Continued)

FOREIGN PATENT DOCUMENTS

| JP | 2002-065682 A | 3/2002 |
| WO | WO 2009/111319 A1 | 9/2009 |
| WO | WO2017/186802 A3 | 11/2017 |

OTHER PUBLICATIONS

International Preliminary Examining Authority, "Search Report" in application No. PCT/EP2017/059952, dated Jul. 6, 2018, 15 pages.

(Continued)

*Primary Examiner* — Julianna N Harvey
(74) *Attorney, Agent, or Firm* — Hickman Palermo Becker Bingham LLP; Malgorzata A. Kulczycka

(57) ABSTRACT

The invention concerns an inner fixation device for the correction of axial deformities of a limb, for example a long limb, of the type comprising at least one plate (2, 2') for epiphysiodesis with at least a pair of lobes (3,4) each provided with a through hole (7) to be laterally fixed to a bone portion or to a long bone head. Advantageously, the device (1) comprises one second plate (12, 12') placed on the opposite side of the bone portion with respect to said at least one plate (2, 2') and connected to that by at least one rod (15) passing through the bone portion. The rod (15) is extended through the bone in parallel to an epiphyseal plate and it has opposite extremities (16,17) connected to the plates (2,2';

(Continued)

2,12') to keep them close to the bone and to stop the bone growth in one central portion of the bone.

9 Claims, 10 Drawing Sheets

(56) References Cited

U.S. PATENT DOCUMENTS

| | | | |
|---|---|---|---|
| 2009/0234462 A1* | 9/2009 | Mullaney | A61B 17/683 623/47 |
| 2013/0096559 A1 | 4/2013 | Katrana et al. | |
| 2015/0142065 A1* | 5/2015 | Schonhardt | A61B 17/8047 606/289 |

OTHER PUBLICATIONS

European Patent Office, "Search Report" in application No. PCT/EP2017/059952, dated Oct. 26, 2017, 3 pages.

* cited by examiner

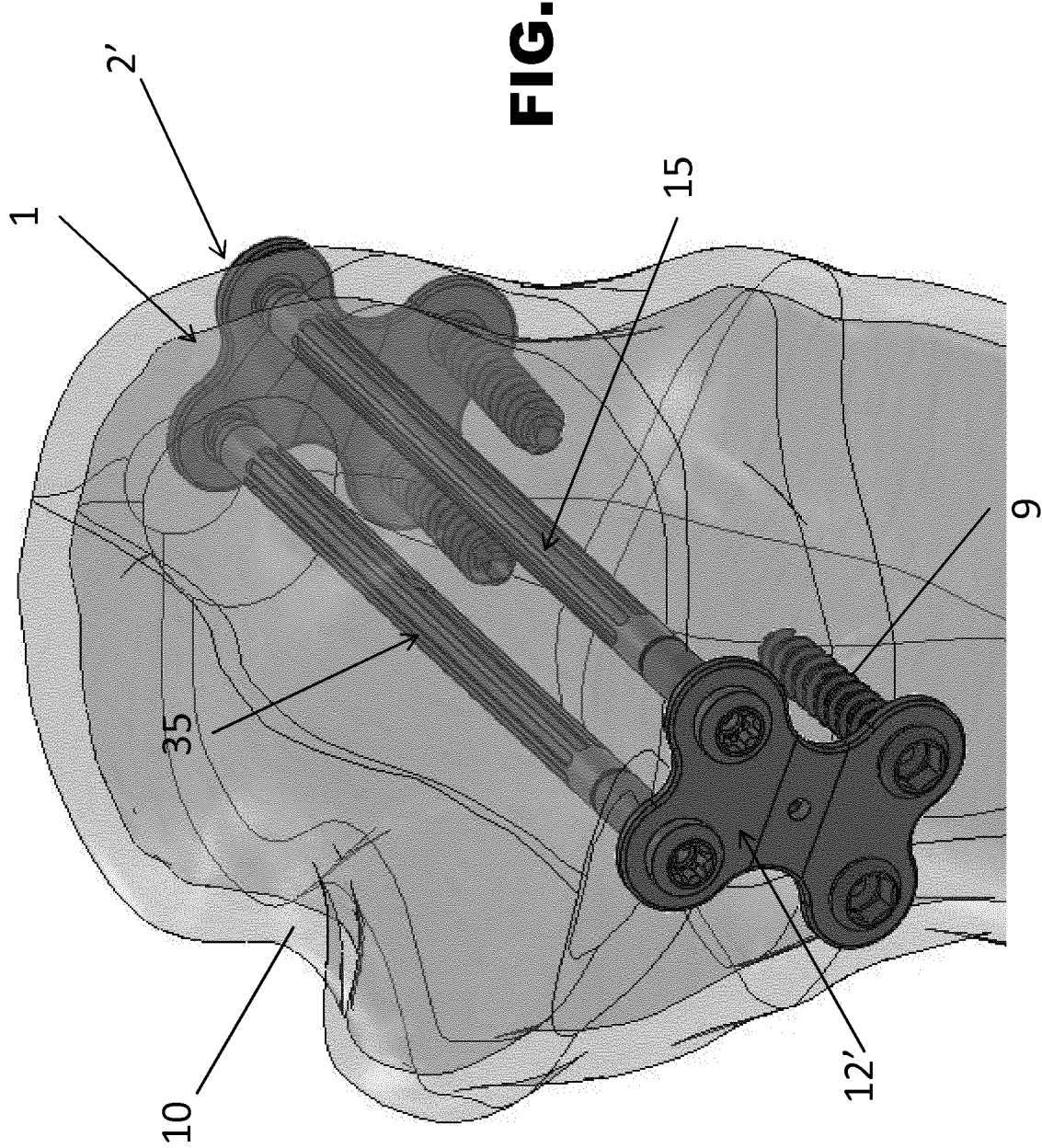

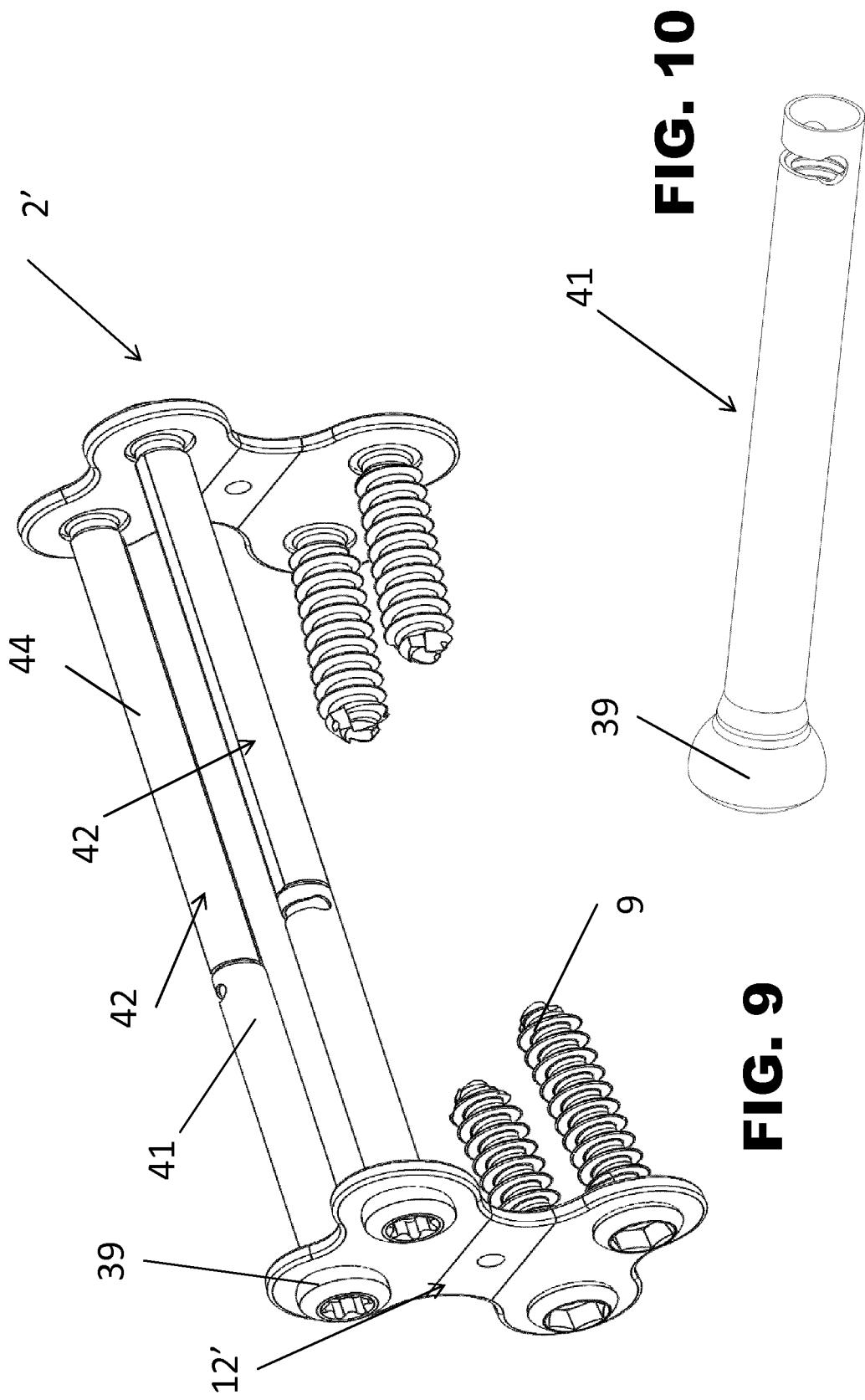

INNER FIXATION DEVICE FOR THE TREATMENT OF A LIMB, IN PARTICULAR THE FEMUR DISTAL PORTION OR TIBIA PROXIMAL PORTION

The present invention concerns an inner fixation device for the treatment of a limb, in particular for the treatment of the femur distal portion or tibia proximal portion.

The invention concerns, in particular but not exclusively, a fixation device intended to treat, heal and correct axial deformities of a limb, for example a lower limb, and of the type comprising at least one plate for epiphysiodesis with at least a pair of lobes provided with a respective through hole to be laterally fixed to a bone portion or to a long bone head.

FIELD OF APPLICATION

In the technical field of the present invention, it is known dealing with axial deformities of the lowers limbs which consist respectively in an inward or outward deviation of the limb axis. We talk about valgus knee in one case, while it is defined varus knee in the other case.

A knee is defined valgus when the femur and the tibia are not perfectly aligned thus they form a laterally open angle. Such a condition is commonly speaking described as "x-shaped legs".

Actually, these are physiological deformities and they occur in a determined period of growth, for example within the first thirty-six months of age for the varus knee and within the first seven years of age for the valgus knee.

Out of these two periods of age, it is appropriate to surgically treat and correct these deformities through operations called: temporary asymmetric epiphysiodesis. As a matter of fact, in case an idiopathic valgus knee is maintained up until the adolescence age, it may cause remarkable aesthetic damages as well as walking problems together with front knee pain and femoral-patellar problems.

The epiphysiodesis operation enables to selectively stop the bone growth in the internal part of the knee, so as to allow a progressive self-correction of the deficiency as growth continues until it is completed.

Epiphysiodesis surgical operations are performed at an age when the epiphyseal plates of the proximal tibia and/or of the distal femur are still active, taking care of not overcoming the cartilage calcification age, in other words two years before this event. In clinical practice it is suggested to perform epiphysiodes at the age of about 11-12 for females and 12-13 for males.

A medial epiphysiodesis operation for the valgus knee, or lateral epiphysiodesis operation for the varus knee is performed under general anaesthesia through the application of small fixation devices as clevis or plates arranged on top of the epiphyseal plate of the distal femur and/or the proximal tibia, in an external or inner region depending if it is a varus or valgus condition.

About one year or one year and a half after the operation, the deformity is usually completely corrected and the fixation devices must be removed.

Prior Art

In the here enclosed FIG. 1, an X-ray image of a valgus knee is shown on which a unilateral medial plate has been applied that is kept in position by bone screws. The plate is basically eight-plate configured or configured like a biscuit and it is for example disclosed in the U.S. Pat. No. 7,811,312 by Stevens.

The epiphysiodesis with unilateral medial plate represents a simple though excellent alternative to more important corrective osteotomy operations. However, a sufficient residual quantity of epiphyseal plate must remain in the distal part of the femur and in the proximal part of the tibia in order for this surgical technique to be successful.

It is important that the plate is arranged on top of the tibial plateau cartilage so that the two screws implanted in the bone are respectively over and below the cartilage and that they do not interfere with the latter during the bone growth.

In case it is necessary to reduce the growth of one limb in relation to the other, it is necessary to apply the plate on both sides of the bone.

However, in this case, the slowing down of the bone growth is not homogeneous for the whole tibial plate as it would be necessary.

Despite the fact that screws are an interference element, it has been proved that the bone growth is not completely blocked in a satisfactory way.

In particular, in the case of the tibia, it has been ascertained a growth of the tibial spine, basically in the middle of the bone, which determines a further bone deformation.

Presently, the prior art has not developed any solution to overcome, limit or avoid such an effect.

The technical problem underlying the present invention is devising an inner fixation device for the treatment of a limb, for instance for the correction of axial deformities of a limb, in particular deformities of the femoral distal portion or of the tibial proximal portion, the device having structural and functional characteristics to enable to stop the bone growth in one central portion of the bone, at least at one side of the cartilage.

Another object of the invention is devising an inner fixation device that can be easily removed at the end of the treatment period.

An additional object of the invention is allowing the use of a conventional plate for epiphysiodesis.

SUMMARY OF THE INVENTION

The underlying idea of a solution of the present invention is providing a double epiphysiodesis plate at opposite parts with respect to the bone portion or head to be treated and a rigid link between the plates crossing the bone portion or head to stop the bone growth in one central portion of the bone.

On the basis of such an idea of solution, the technical problem is overcome by a device of the previously indicated type and characterized in that it comprises a second plate arranged at the opposite part of the bone portion with respect to said at least one plate and linked to it by means of at least a rod crossing the bone portion.

Such rod is extended through the bone in parallel to the epiphyseal plate and it has opposite extremities connected to the plates to keep them close to the bone. This rod may be intended as a tie-rod owing to the opposite extremities bound to the plates; however, this not necessarily its function.

In a preferred embodiment, the fixator comprises at least two tie-rods extending parallel to each other.

Furthermore, both the first and the second plate are four-lobed with lobes provided with a respective through hole and at least two lobes are bound to a corresponding rod extremity.

Fixation means are provided too on at least one extremity of said rod, while fixation counter-means are provided in association with said at least one plate or said second plate to connect permanently the two plates through the rod.

The fixing means are for example the threaded extremity of said at least one rod.

At least one of said counter-means is a screw with a head and an internally threaded squat stem; said head having a recessed seat shaped for receiving a manoeuvring tool.

The stem has a threaded constraint with a tie-rod extremity.

In a dual way, at least one of said counter-means is a screw with a head and an externally threaded squat stem having a constraint with a recessed extremity of said rod.

In alternative, at least one of said fixing counter-means is a screw without stem, with a head equipped with a through hole with an inner thread and allowing access and coaxial with a lowered seat for receiving a manoeuvring tool.

It must be noted that said at least one rod is a solid stem covered by a covering sheath.

In alternative, the rod comprises a couple of components, a stem on whose free extremity the extremity of a hollow tubular body is bayonet-fixed, the stem and the hollow tubular body having opposite extremities conformed as a screw head.

The features and the advantages of the inner fixing device according to the invention will be evident from the hereinafter disclosure of an exemplary non-limiting embodiment, referring to the enclosed drawings.

BRIEF DESCRIPTION OF THE DRAWINGS

FIG. 5 shows a perspective and schematic view of an embodiment of the inner fixation device according to the invention;

FIG. 9 shows a perspective view of a second embodiment of the inner fixator of the present invention;

FIG. 10 shows a perspective view of an inner fixation component of FIG. 9;

DETAILED DESCRIPTION

Figure 1:
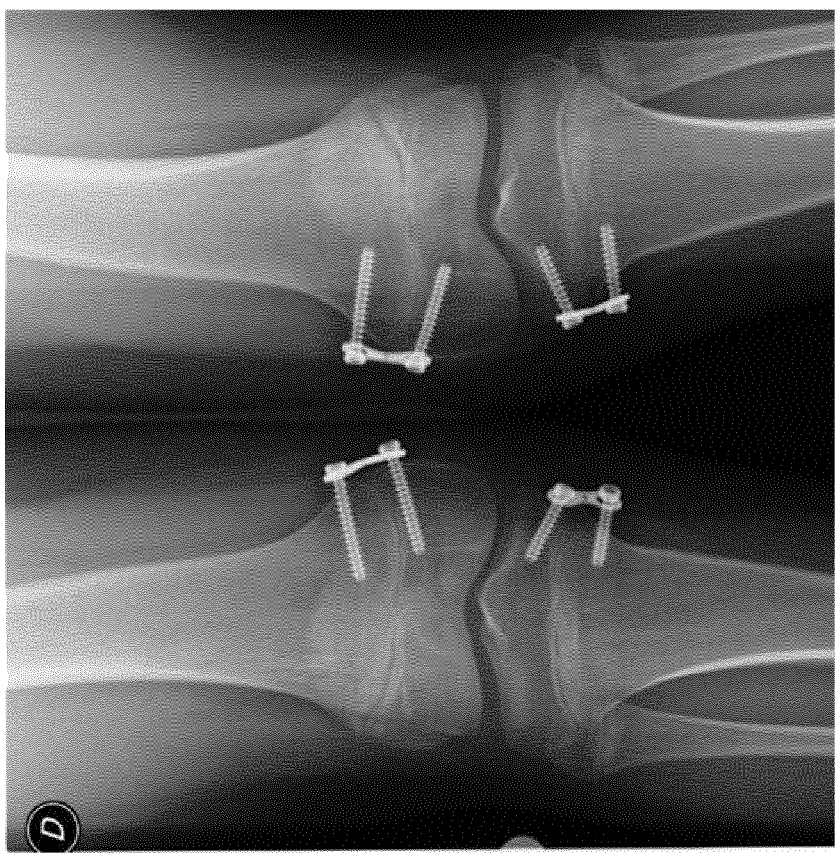
FIG. 1 shows an X-ray image of a patient suffering from valgus knee and treated according to the prior art.

Referring to such figures, by 1 it is globally and schematically indicated an inner fixation device made according to the present invention for treating, healing and correcting axial deformities of a limb, in particular deformities of the femur distal portion or of the tibia proximal portion.

More in particular, we might state that the invention intends to correct paediatric knee valgus-varus conditions through temporary arthrodesis of a bone methaphyses, in particular of the femur distal methaphyses or of the tibia proximal methaphyses.

Device 1 comprises at least a plate 2 for epiphysiodesis. Plate 2 is provided with a pair of lobes 3, 4, each provided with a through hole 7 for the passage of a bone fixing screw 9. Plate 2 is intended to be laterally fixed to a bone portion, or more precisely but not exclusively, to a long bone head 10, for example a limb bone as the femur distal head or the tibia proximal head.

Furthermore, plate 2 is positioned so as to be arranged over the cartilage present in the bone head, as for example, the cartilage in a tibial plateau, as provided in the applications for epiphysiodesis shown in FIG. 1.

Plate 2 is commonly fixed to the bone head 10 through a pair of screws 9 inserted in the bone through the through holes 7 in lobes 3 and 4 of the plate thereof. Screws 9 are commonly inserted in the bone cortical all over their length so that only the screw head 8 is accessible and abutting against the plate portion around the hole 7.

Figure 2:
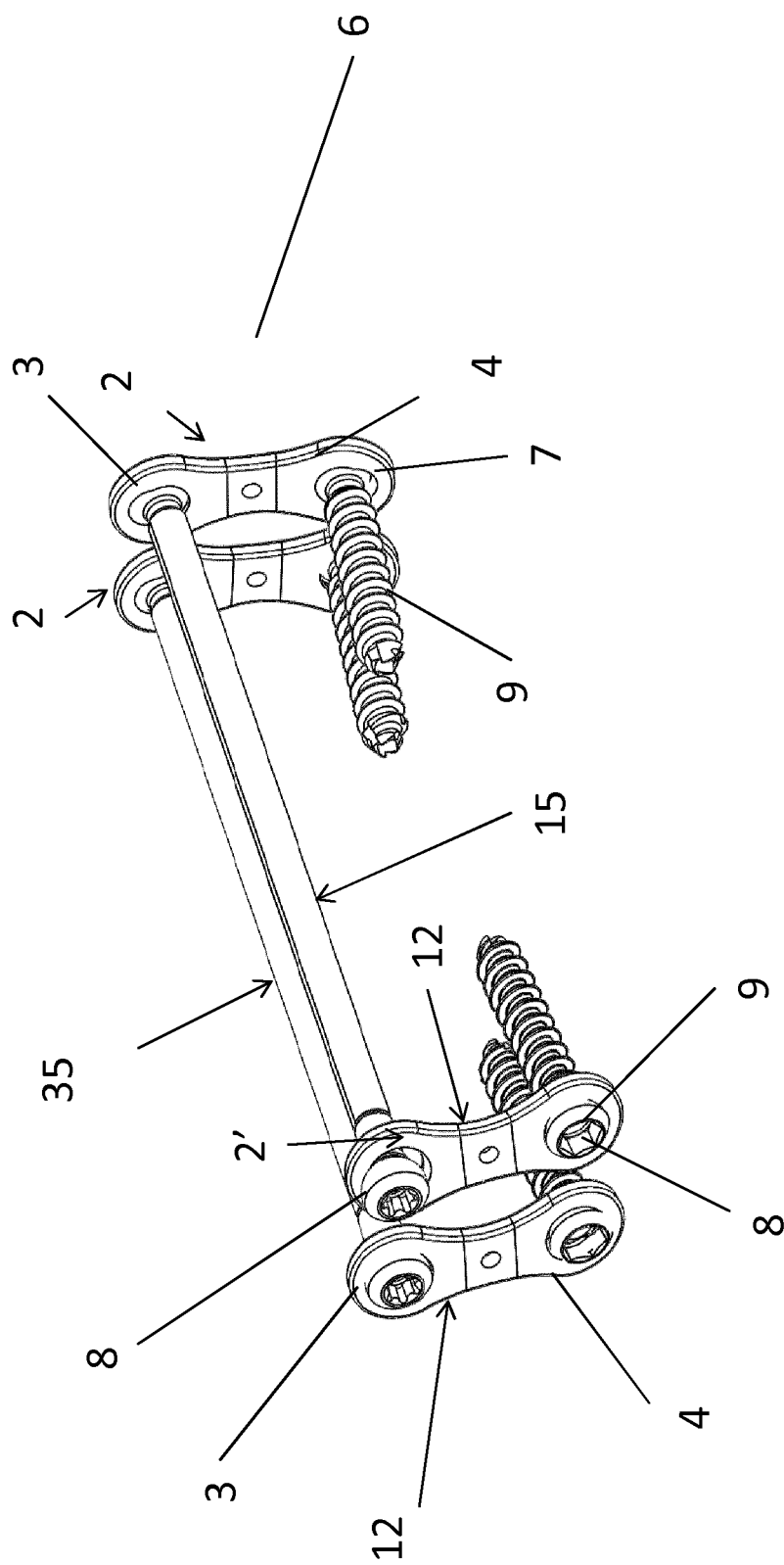
FIG. 2 is a perspective view of a first embodiment of the fixing device according to the invention.

Plate 2 is commonly of the eight-plate type with only two lobes 3 and 4, as shown in FIG. 2. However, the invention also provides for a different conformed plate to be used such as for example a four-lobe plate 2' with lobes 3, 4, 5 and 6 substantially arranged cross-vaulted and at rounded corners of a quadrilateral shape. However, in this case too, each of the lobes 3, 4 5 or 6 is provided with a through hole 7, slightly countersunk, for example for inserting a bone fixing screw 8.

Figure 4:
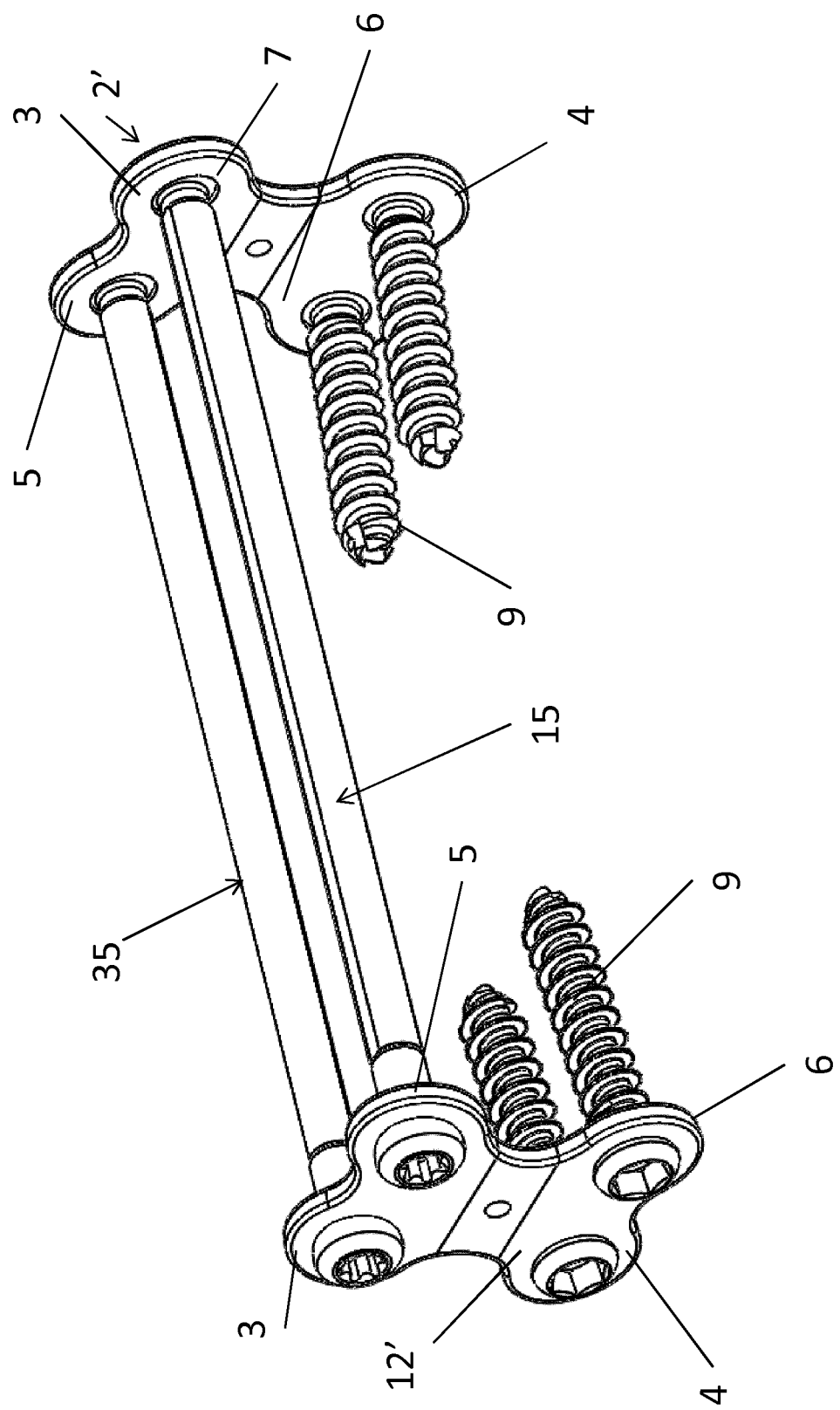
FIG. 4 shows a perspective view of the inner fixation device according to the present invention.

Advantageously, according to the invention, the inner fixing device 1 comprises a second plate 12 for epiphysiodesis arranged at a direction opposite to the first plate with respect to the bone portion or to the bone head they are associated to. Plate 12 may be eight-plate conformed with only two lobes, as plate 2, or it may be a four-lobe plate, as shown in FIGS. 4 and 5.

Furthermore, the two plates 2, 12 or 2', 12' are linked each other through at least one rod 15 which crosses the bone portion or head 10 they are associated to.

Advantageously, the rod 15 extends as a bridge on the nearby cartilage.

In other words, the device 1 of the present invention is an inner fixator comprising two opposite epiphyodesis plates 2, 12 or 2', 12', elongated in the cranium-caudal direction and placed at opposite sides of the bone, and at least one rod 15, extending through the bone and having opposite extremities linked to the plates to keep them close to the bone and to stop the bone growth in one central portion of the bone.

Rod 15 may be intended as a tie-rod owing to its opposite extremities 16, 17 bound to the plates 2, 12 or 2', 12'; however, the rod 15 must not necessarily play the function of tie-rod because it may even be considered a strut.

In any case, the previously described configuration with the rod 15 having opposite extremities connected to the plates has the great advantage to bind the plates 2 or 2' and 12 or 12' one another and not necessarily to the bone or to the bone head they are intended for.

Rod 15 is substantially a rod crossing the bone in a through hole previously obtained by means of an appropriate tool, for example a drill bit, not shown since it is conventional.

In one first embodiment, for example shown in FIG. 2, the rod 15 is an elongated stem 27 with cylindrical shape.

Rod 27 may be solid or hollow depending on the needs. A solid stem provides more rigidity to the overall structure of the inner fixation device.

Rod 15 opposite extremities 16, 17 are provided with fixing means 20 to bind such extremities to a respective plate 2, 12 or 2' and 12'. Fixing counter-means 40 are also provided to cooperate with the fixing means 20 in binding the plates 2, 12 or 2', 12' between them and the rod or rod 15.

At least one fixing bone screw 9 is inserted in the hole 7 of the plate 2, 2'; or 12, 12 not having a constraint with said at least one rod 15.

In one embodiment shown in FIG. 4, there are two rods 15 and 35 and they are arranged parallel to each other. In the embodiment of FIG. 4, the two rods are bound at the upper lobes 3 and 5 of the plates 2' and 12', while the lower lobes 4 and 6, with their respective through holes 7, have fixing bone screws 9.

Thereby the pair of rods 15 and 35 is positioned at the same side with respect to the cartilage, as shown in the application of FIG. 5.

Figure 11:
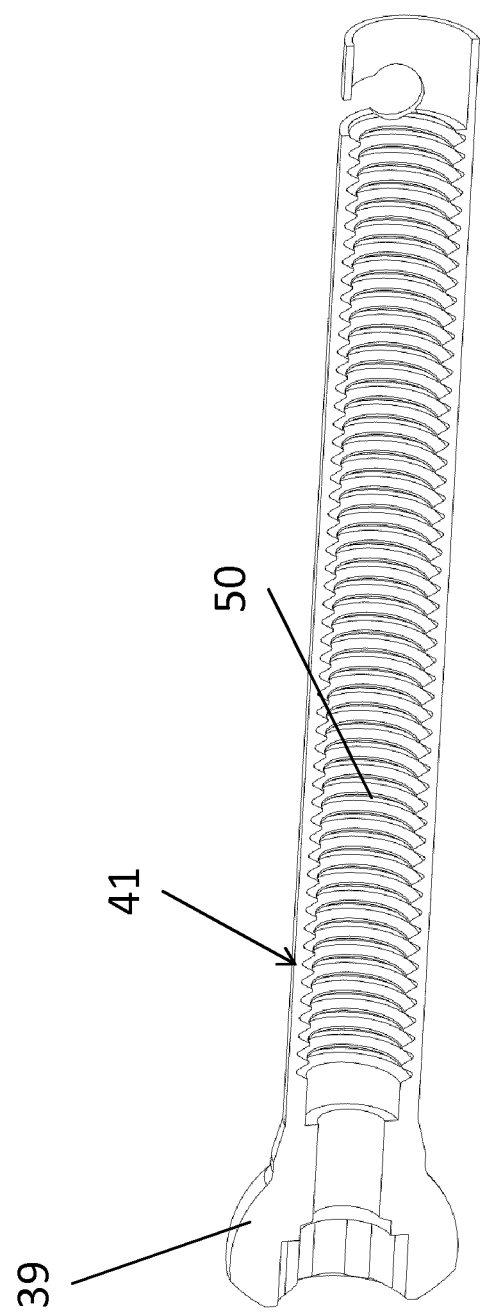
FIG. 11 shows a perspective view in longitudinal section of the component of FIG. 10.
Figure 12:
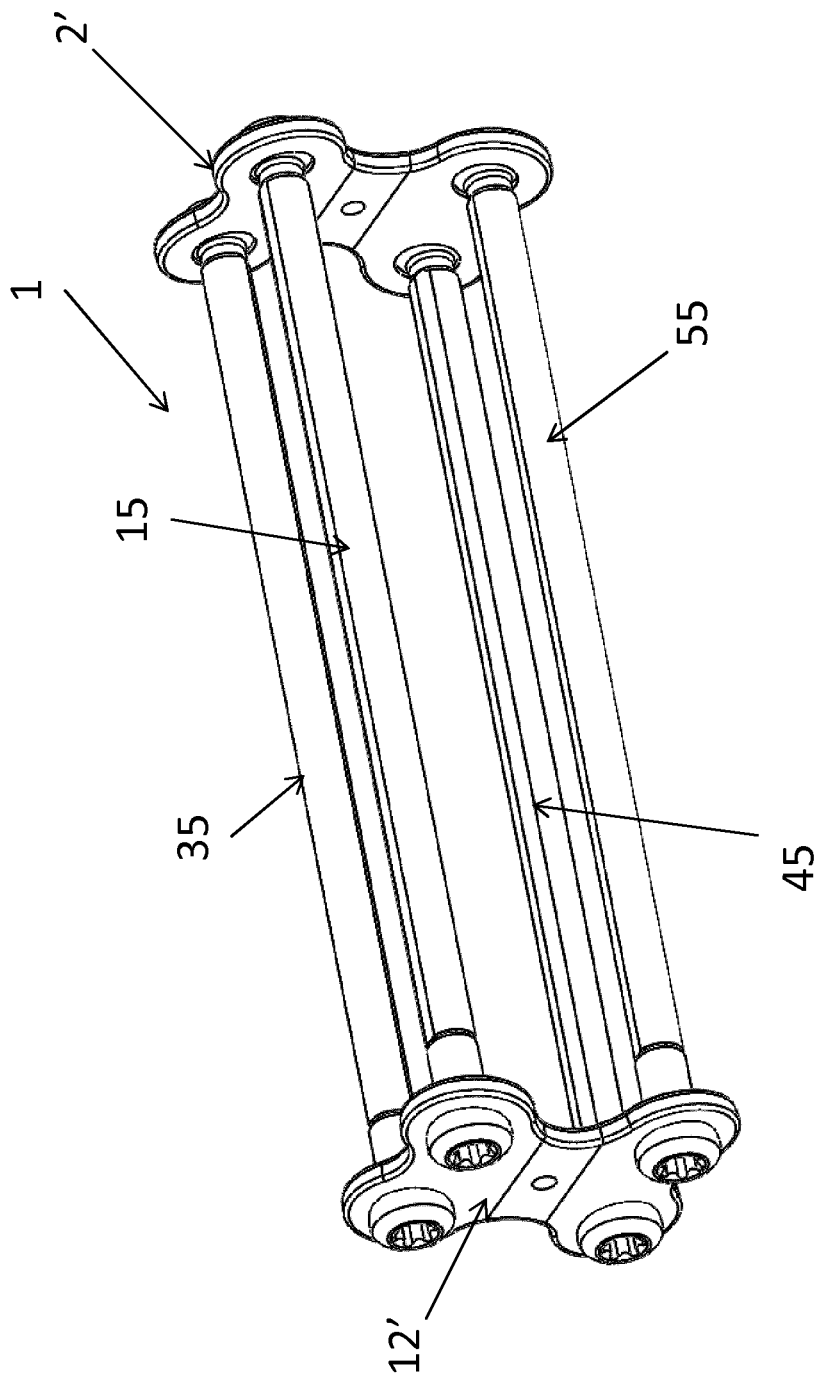
FIG. 12 shows a perspective view of an additional embodiment of the inner fixation device according to the invention.

In one alternative embodiment, as for example shown in FIG. 11, there are four tie-rods 15, 35, 45 and 55 and they are arranged and place side by side in pairs at opposite parts of the cartilage.

Substantially, each tie-rod extremity is associated through fixation means 20 and counter-means 40 to one corresponding lobe of the plate 2' or 12'.

We will hereinafter see the different types of fixing means 20 and counter-means 40.

The fixing means 20 are for example one threaded extremity of the rod 15.

In the embodiment of Figures from 2 to 5, the rod 15 has one threaded extremity 18 and one opposite extremity 17 shaped as a screw head. However, nothing prevents both extremities 16 and 17 from being threaded.

Figure 6:
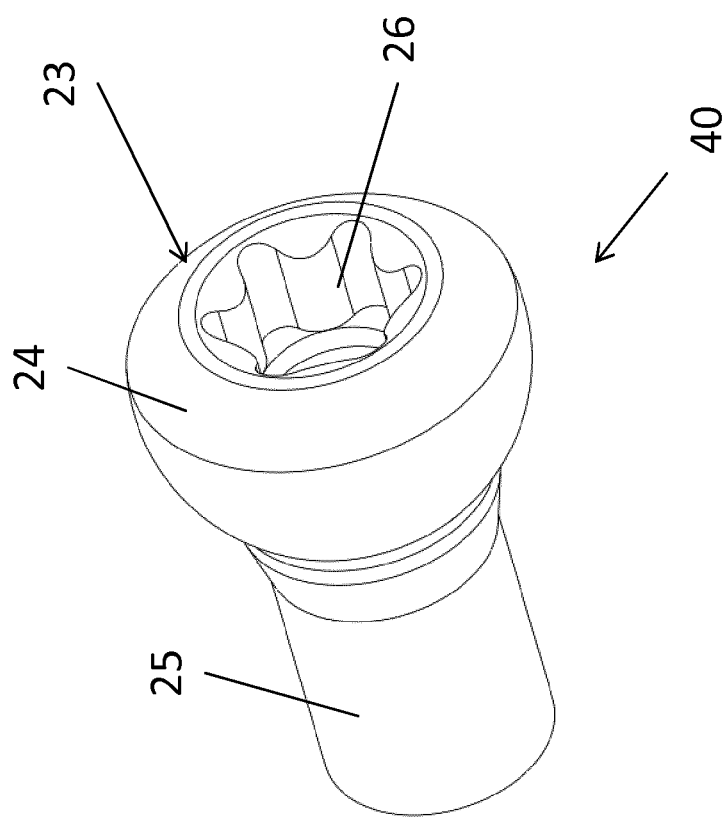
FIG. 6 shows a perspective view of a detail of the inner fixation device according to the invention.

The fixing counter-means 40 may be implemented in different ways as for example the solution illustrated in FIG. 6 which provides a screw 23 with an enlarged head 24 and an internally threaded squat stem 25. The head 24 has greater radial sizes than the stem 25 and provides for a recess seat 26 shaped to receive a manoeuvring tool such as an hex key, not shown in the drawings.

The shape and the dimensions of the shaped seat 26 is compatible with the overall dimensions of the head 24.

Furthermore, in the embodiment shown in Figures from 2 to 5, at least one extremity 16 of the rod 15 has a thread 18 on which the inner threaded portion of the squat stem 25 of the screw 23 may be screwed.

However, an expert in the field knows well that both extremities 16 and 17 of the rod 15 may be provided with a thread 18 bound to a corresponding screw 23 of the previously described type.

However, as already said, in the preferred embodiment the rod 15 provides for a single extremity 16 with thread 18 while the opposite extremity 29 is piece conformed as a screw head, at all similar to the screw 23 head 24, with recess seat 26 for the manoeuvring tool.

Figure 8:
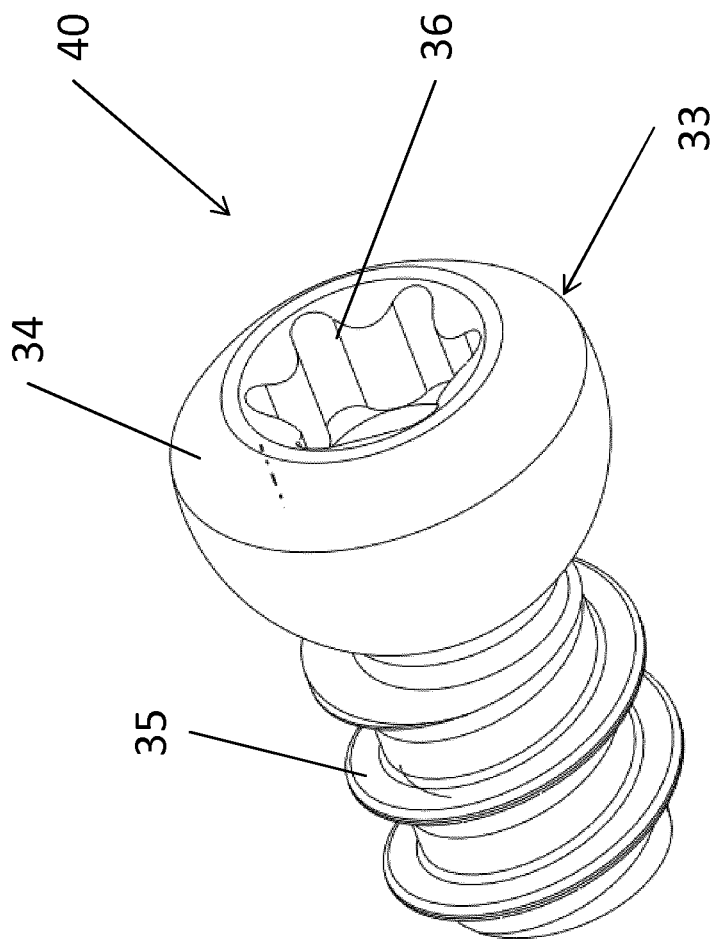
FIG. 8 shows a perspective view of a further alternative detail of the inner fixation device according to the invention.

In one embodiment which we may define as dual, and which is illustrated in FIG. 8, a screw 33 with an enlarged head 34 and an externally threaded squat stem 35 is provided as one of the fixing counter means 40.

In this case as well the head 34 has greater radial sizes than the stem 35 and provides for a recess seat 36 shaped to receive a manoeuvring tool such as an hex key, not shown in the drawings.

The stem 35 is engaged with a conjugated recessed seat and threaded at one extremity of said rod 15.

Figure 7:
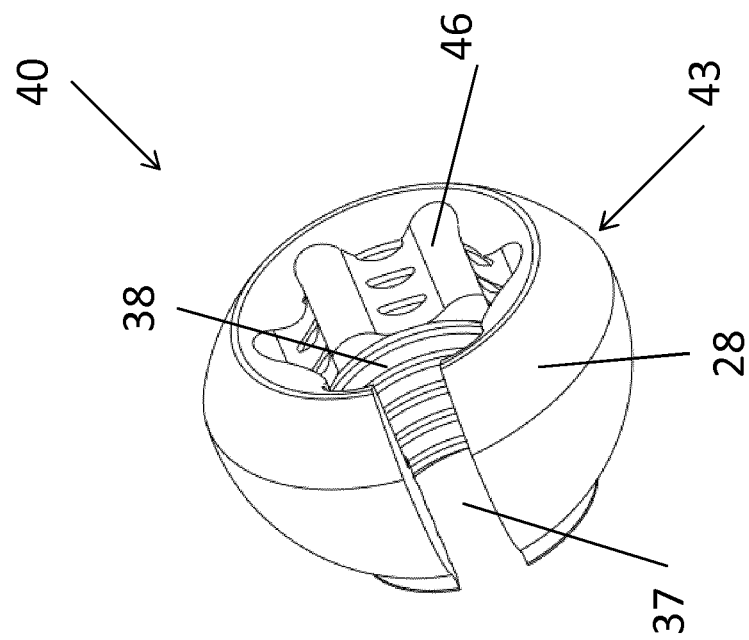
FIG. 7 shows a perspective view of an alternative detail of the inner fixation device according to the invention.

In one additional embodiment of the fixing counter-means 40, shown in FIG. 7, a screw 46 head 28 is without stem and has a through hole 37 that is centrally and internally provided with a thread 38. Such screw may be compared to a simple fixing nut except for the head 43 provided with a recessed seat 46 for inserting a manoeuvring tool.

The hole 37 is coaxial and allowing access to the recessed seat 46.

Screws 23, 33 or 43 substantially have a spherical head so as to guarantee an angularly directable constraint in a respective countersunk hole 7 of the plates 2, 2', 12 or 12'.

Figure 3:
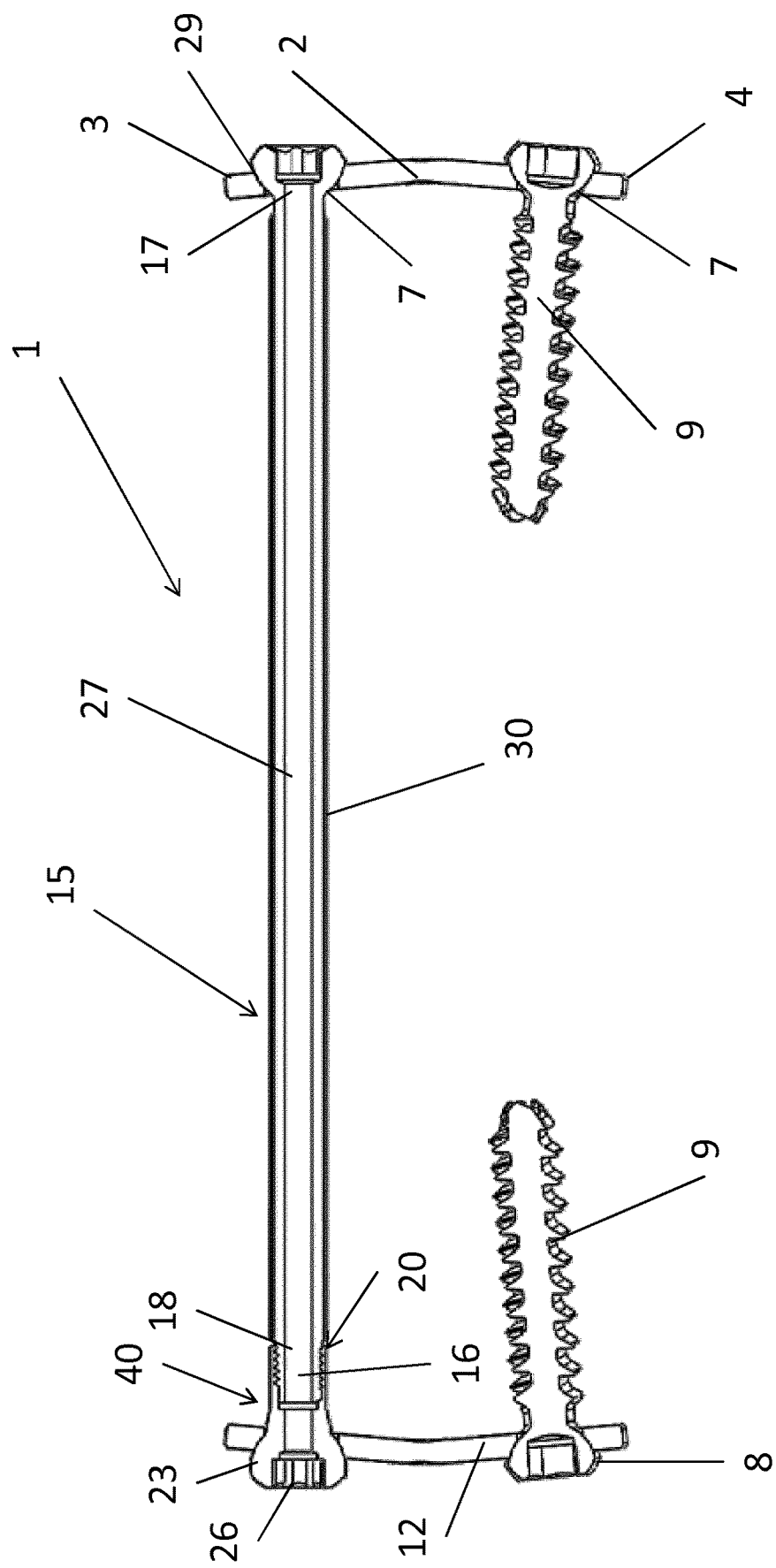
FIG. 3 shows a side view of an inner fixation device according to the present invention.

It is also possible to provide for a covering sheath 30 or case for the stem 27, visible in FIG. 3. The sheath 30 is tubular cylindrical and long enough to cover the extension of the tie-rod or rod 15.

The tubular case 30 is made of a predetermined material and of a predetermined external surface irregularity, to cover a stem portion of a predetermined length.

In one additional embodiment, for example shown in FIGS. 9 and 10, the rod 15 or the rod 35, or both rods 15, 35 are conformed so as to include the fixing means 20 and counter-means 40.

In the embodiment illustrated in FIGS. 9 and 10, a rod 42 comprises two portions 41 and 44 each other attachable and each provided with a respective structure head 39 similar to the screws 23, 33 and 43 heads.

More in particular, the semi-rod 44 portion is a stem of a predetermined length having an extremity 39 shaped as a screw head.

The stem or semi-rod 44 opposite extremity is shaped to be coupled to the free extremity of the other rod 42 portion 41 by means of one thread. The portion 44 free extremity is provided with a thread substantially similar to the one disclosed in the first embodiment referring to the rod 15 extremity 16.

The tie-rod 42 portion 41 has one extremity shaped as a screw head 39. The two rod 41, 44 portions are of a predetermined length as required by the orthopedic surgeon for his implanting convenience needs. For example, the shortest portion 41 may be equal to one third of the whole length of one rod 15 disclosed in the first embodiment, while the remaining portion 42 may be as long as two thirds of the rod 15. Obviously other proportions may be adopted.

In the herein described preferred embodiment, without limitation, the portion 41 is tubular and has an inner longitudinal thread 50 which substantially extends along the whole length of portion 41. The inner thread 50 is intended to receive and engage with the free extremity of the other rod portion 44. By screwing the threaded shaped tube 41 through the screw or the threaded terminal portion of the semi-rod 44, the load causes a flexion of the section which applies a friction force on the rotation of the screw thus blocking it.

It must be added that each plate 2, 2', 12 or 12' comprises a guiding hole in the middle position to set the position of the bone cartilage they must be associated to.

Tests implemented at the Applicant's have assessed that the inner fixation device of the present invention is able to block the growth of the knee medial section with respect to the lateral one thus resulting in a more normal reconstruction of the angular ratio between femur and tibia.

It is necessary patients are carefully followed-up at three/six-month-intervals in order to check the deformity correction.

The invention claimed is:

1. An inner fixation device for the treatment of a limb, the inner fixation device comprising:
   a first plate for epiphysiodesis with at least a pair of lobes each provided with a through hole adapted to be laterally fixed to a bone portion or to a long bone head, a second plate for epiphysiodesis adapted to be placed on the opposite side of the bone portion with respect to said first plate,
wherein the first plate and the second plate are identical in shape;
at least one connection element adapted to pass through the bone portion extending through the bone portion in parallel to an epiphyseal plate;
said second plate being connected to said first plate by said at least one connection element;
said at least one connection element having opposite extremities connected to the plates to keep them close to the bone portion and to stop a bone growth in one central portion of the bone portion;
said at least one connection element including a pair of semi-rod components; each semi-rod component, of the pair of semi-rod components, having two extremities one of which is threaded and another is shaped to be coupled to a free extremity of another semi-rod of the pair of semi-rod components.

2. The inner fixation device according to claim 1, wherein both the first plate, and the second plate are four-lobed with lobes provided each with a through hole and with at least two lobes that are bound to a corresponding connection element extremity.

3. The inner fixation device according to claim 1, further comprising: fixation means provided on at least one extremity of said at least one connection element, and fixation counter-means provided in association with said first plate or said second plate to connect permanently the first plate with the second plate through the at least one connection element.

4. The inner fixation device according to claim 3, wherein said fixation means is a threaded extremity of said at least one connection element.

5. The inner fixation device according to claim 3, wherein at least one of said fixation counter-means is a screw with a head and an internally threaded squat stem; said head having a recessed shaped seat for receiving a manoeuvring tool.

6. The inner fixation device according to claim 5, wherein said internally threaded squat stem has a threaded constraint with a tie-rod extremity.

7. The inner fixation device according to claim 3, wherein said fixation counter-means is a screw with a head and an externally threaded squat stem having a constraint with a recessed extremity of said at least one connection element.

8. The inner fixation device according to claim 3, wherein said fixation counter-means is a screw without a stem, with a head equipped with a through hole with an inner thread for allowing access and coaxial with a lowered seat for receiving a manoeuvring tool.

9. The inner fixation device according to claim 1, further comprising: at least one fixation bone screw inserted in a plate hole of the first plate and not having a constraint with said at least one connection element.

* * * * *